United States Patent [19]

Smith

[11] 4,080,373

[45] Mar. 21, 1978

[54] 13,14 DEHYDRO PGF$_3$ COMPOUNDS

[75] Inventor: Herman W. Smith, Kalamazoo, Mich.

[73] Assignee: The Upjohn Company, Kalamazoo, Mich.

[21] Appl. No.: 742,786

[22] Filed: Nov. 18, 1976

Related U.S. Application Data

[62] Division of Ser. No. 657,738, Feb. 13, 1976, Pat. No. 4,018,803.

[51] Int. Cl.$^2$ .............................................. C07C 177/00
[52] U.S. Cl. ............................. 260/408; 260/410.9 R; 260/413; 260/514 D; 560/121
[58] Field of Search .............. 260/468 D, 514 D, 408, 260/410.9 R, 413

[56] References Cited

U.S. PATENT DOCUMENTS 4,013,695  3/1977  Lin ..................................... 260/410.9

OTHER PUBLICATIONS

Fried et al., J. Med. Chem. 16, 429 (1973).
Cooper et al., Proc. Nat. Acad. Sci., 70, 1579 (1973).

*Primary Examiner*—Robert Gerstl
*Attorney, Agent, or Firm*—Robert A. Armitage

[57] ABSTRACT

This invention comprises certain analogs of the prostaglandins in which the double bond between C-13 and C-14 is replaced by a triple bond. Also provided in this invention are novel chemical processes and novel chemical intermediates useful in the preparation of the above prostaglandin and analogs. These prostaglandin analogs exhibit prostaglandin-like activity, and are accordingly useful for the same pharmacological purposes as the prostaglandins. Among these purposes are blood pressure lowering, labor induction at term, reproductive-cycle regulation, gastric antisecretory action, and the like.

48 Claims, No Drawings

COMPOSITION AND PROCESS

The present application is a divisional application of Ser. No. 657,738, filed Feb. 13, 1976, now issued as U.S. Pat. No. 4,018,803, on Apr. 19, 1977.

The present invention relates to prostaglandin analogs for which the essential material constituting a disclosure therefor is incorporated by reference here from U.S. Pat. No. 4,018,803, issued April 19, 1977.

I claim:

1. A compound of the formula

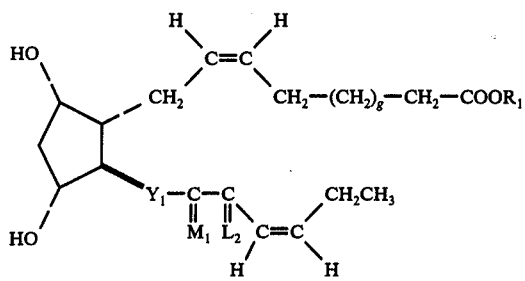

wherein $Y_1$ is —C≡C—;
wherein $g$ is 1, 2, or 3;
wherein $M_1$ is

or

wherein $R_5$ and $R_6$ are hydrogen or methyl, with the proviso that one of $R_5$ and $R_6$ is methyl only when the other is hydrogen;
wherein $L_2$ is

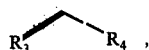

or a mixture of

and

wherein $R_3$ and $R_4$ are hydrogen or fluoro, being the same or different, with the proviso that at least one of $R_3$ and $R_4$ is fluoro; and
wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro or alkyl of 1 to 3 carbon atoms, inclusive, or a pharmacologically acceptable cation.

2. A compound according to claim 1, wherein $g$ is 3.

3. A compound according to claim 2, wherein $R_3$ and $R_4$ are both fluoro.

4. A compound according to claim 3, wherein $R_5$ and $R_6$ are hydrogen.

5. 2a,2b-Dihomo-16,16-difluoro-13,14-didehydro-PFG$_{3\alpha}$, methyl ester, a compound according to claim 4.

6. A compound according to claim 1, wherein $g$ is 1.

7. A compound according to claim 6, wherein both $R_3$ and $R_4$ are fluoro.

8. A compound according to claim 7, wherein $R_5$ and $R_6$ are hydrogen.

9. 16,16-Difluoro-13,14-didehydro-PGF$_{3\alpha}$, methyl ester, a compound according to claim 8.

10. A compound of the formula

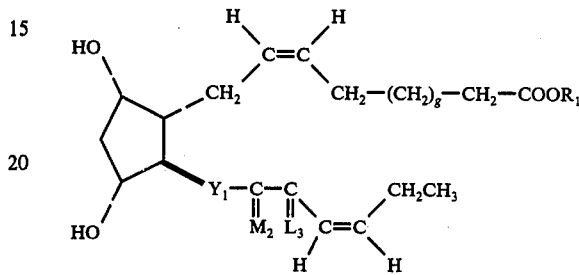

wherein $Y_1$ is —C≡C—;
wherein $g$ is 1, 2, or 3;
wherein $M_2$ is

or

wherein $L_3$ is

or a mixture of

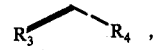

and

wherein $R_3$ and $R_4$ are hydrogen or methyl, being the same or different; and
wherein $R_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro or alkyl of 1 to 3 carbon atoms, inclusive, or a pharmacologically acceptable cation.

11. A compound according to claim 10, wherein $g$ is 1.

12. A compound according to claim 11 wherein at least one of $R_3$ and $R_4$ is methyl.

13. A compound according to claim 12, wherein $R_3$ and $R_4$ are both methyl.

14. A compound according to claim 11, wherein $R_3$ and $R_4$ are hydrogen.

15. 13,14-Didehydro-PGF$_{3\alpha}$, methyl ester, 15-methyl ether, a compound according to claim 14.

16. A compound of the formula

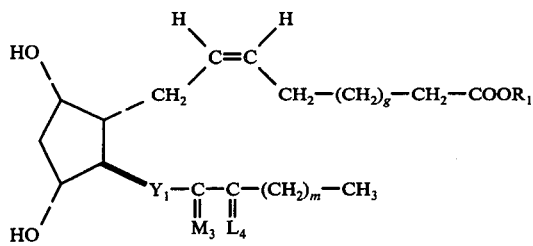

wherein Y$_1$ is —C≡C—;
wherein g is 1, 2, or 3;
wherein M$_3$ is

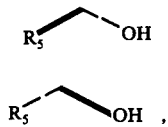

or

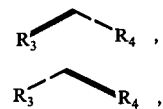

wherein R$_5$ is hydrogen or methyl;
wherein L$_4$ is

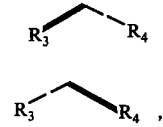

or a mixture of and wherein R$_2$ and R$_3$ are hydrogen or methyl, being the same or different, with the proviso that one of R$_3$ and R$_4$ is methyl; and
wherein R$_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

17. A compound according to claim 16, where g is 3.

18. A compound according to claim 17, wherein R$_3$ and R$_4$ are both methyl.

19. A compound according to claim 18, wherein R$_5$ is hydrogen.

20. 2a,2b-Dihomo-16,16-dimethyl-13,14-didehydro-PGF$_{3\alpha}$, methyl ester, a compound according to claim 19.

21. A compound according to claim 16, wherein g is 1.

22. A compound according to claim 21, wherein R$_3$ and R$_4$ are both methyl.

23. A compound according to claim 22, wherein R$_5$ is hydrogen.

24. 16,16-Dimethyl-13,14-didehydro-PGF$_{3\alpha}$, methyl ester, a compound according to claim 23.

25. A compound of the formula

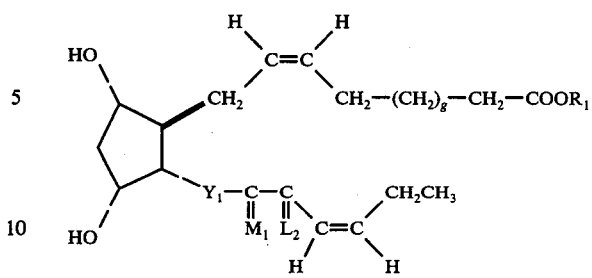

wherein Y$_1$ is —C≡C—;
wherein g is 1, 2, or 3;
wherein M$_1$ is

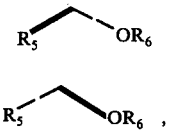

or wherein R$_5$ and R$_6$ are hydrogen or methyl, with the proviso that one of R$_5$ and R$_6$ is methyl only when the other is hydrogen;
wherein L$_2$ is

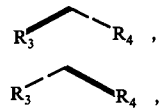

or a mixture of and

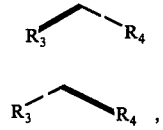

wherein R$_3$ and R$_4$ are hydrogen or fluoro, being the same or different, with the proviso that at least one of R$_3$ and R$_4$ is fluoro; and
wherein R$_1$ is hydrogen, alkyl of 1 to 12 carbon atoms, inclusive, cycloalkyl of 3 to 10 carbon atoms, inclusive, aralkyl of 7 to 12 carbon atoms, inclusive, phenyl, phenyl substituted with 1, 2, or 3 chloro or alkyl of 1 to 3 carbon atoms, inclusive, or a pharmacologically acceptable cation.

26. A compound according to claim 25 wherein g is 3.

27. A compound according to claim 26 wherein R$_3$ and R$_4$ are both fluoro.

28. A compound according to claim 27 wherein R$_5$ and R$_6$ are hydrogen.

29. 2a2b-Dihomo-16,16-difluoro-13,14-didehydro-8β,12α-PGF$_{3\alpha}$, methyl ester, a compound according to claim 28.

30. A compound according to claim 29, wherein g is 1.

31. A compound according to claim 30, wherein both R$_3$ and R$_4$ are fluoro.

32. A compound according to claim 31, wherein R$_5$ R$_6$ are hydrogen.

33. 16,16-Difluoro-13,14-didehydro-8β,12α-PGF$_{3\alpha}$, methyl ester, a compound according to claim 32.

34. A compound of the formula

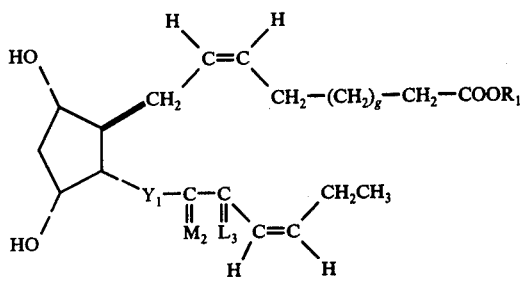

wherein $Y_1$ is —C≡C—;
wherein $g$ is 1, 2, or 3;
wherein $M_2$ is

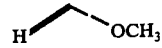

or

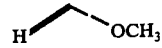, wherein $L_3$ is

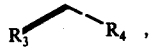,

, or a mixture of

and

, wherein $R_3$ and $R_4$ are hydrogen or methyl, being the same or different; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

35. A compound according to claim 34, wherein $g$ is 1.

36. A compound according to claim 35, wherein at least one of $R_3$ and $R_4$ is methyl.

37. A compound according to claim 36, wherein $R_3$ and $R_4$ are both methyl.

38. A compound according to claim 35, wherein $R_3$ and $R_4$ are hydrogen.

39. 13,14-Didehydro-8β,12α-PGF$_{3\alpha}$, methyl ester, 15-methyl ether, a compound according to claim 38.

40. A compound of the formula

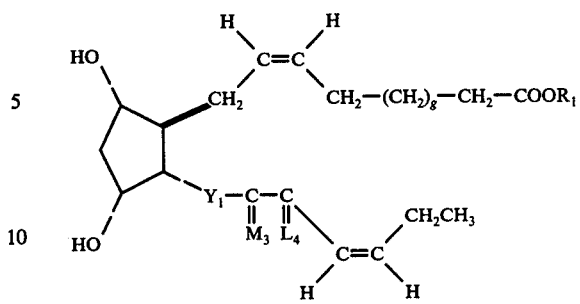

wherein $Y_1$ is —C≡C—;
wherein $g$ is 1, 2, or 3;
wherein $M_3$ is

or

, wherein $R_5$ is hydrogen or methyl;
wherein $L_4$ is

,

, or a mixture of

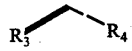

and

, wherein $R_3$ and $R_4$ are hydrogen or methyl, being the same or different, with the proviso that one of $R_3$ and $R_4$ is methyl; and
wherein $R_1$ is hydrogen, alkyl of one to 12 carbon atoms, inclusive, cycloalkyl of 3 to 10 carbon atoms, inclusive, aralkyl of 7 to 12 carbon atoms, inclusive, phenyl, phenyl substituted with one, two, or three chloro or alkyl of one to 3 carbon atoms, inclusive, or a pharmacologically acceptable cation.

41. A compound according to claim 40, wherein $g$ is 3.

42. A compound according to claim 41, wherein $R_3$ and $R_4$ are both methyl.

43. A compound according to claim 42, wherein $R_5$ is hydrogen.

44. 2a,2b-Dihomo-16,16-dimethyl-13,14-didehydro-8β,12α-PGF$_{3\alpha}$, methyl ester, a compound according to claim 43.

45. A compound according to claim 40, wherein $g$ is 1.

46. A compound according to claim 45, wherein $R_3$ and $R_4$ are both methyl.

47. A compound according to claim 46, wherein $R_5$ is hydrogen.

48. 16,16-Dimethyl-13,14-didehydro-8β,12α-PGF$_{3\alpha}$, methyl ester, a compound according to claim 47.

* * * * *